United States Patent
Kurtis et al.

(10) Patent No.: US 9,283,264 B2
(45) Date of Patent: Mar. 15, 2016

(54) SCHISTOSOMA VACCINE

(75) Inventors: Jonathan Kurtis, Providence, RI (US); Mario Jiz, Providence, RI (US); Haiwei Wu, Lincoln, RI (US); Sunthorn Pond-Tor, Cranston, RI (US)

(73) Assignee: Rhode Island Hospital, Providence, RI (US)

( * ) Notice: Subject to any disclaimer, the term of this patent is extended or adjusted under 35 U.S.C. 154(b) by 945 days.

(21) Appl. No.: 12/864,041

(22) PCT Filed: Nov. 5, 2008

(86) PCT No.: PCT/US2008/012486
§ 371 (c)(1),
(2), (4) Date: Feb. 13, 2012

(87) PCT Pub. No.: WO2009/061407
PCT Pub. Date: May 14, 2009

(65) Prior Publication Data
US 2012/0128721 A1    May 24, 2012

Related U.S. Application Data

(60) Provisional application No. 61/002,070, filed on Nov. 5, 2007.

(51) Int. Cl.
*A61K 39/002* (2006.01)
*A61K 39/00* (2006.01)

(52) U.S. Cl.
CPC ... *A61K 39/0003* (2013.01); *A61K 2039/55505* (2013.01); *A61K 2039/55566* (2013.01)

(58) Field of Classification Search
None
See application file for complete search history.

(56) References Cited

PUBLICATIONS

Pearce et al. (PNAS 85:5678-5682, 1988).*
Nara et al. (Internat. Immunol., 6:963-971, 1994).*
Sambrook et al. (Molecular Cloning, a Laboratory Manual, vol. 3, Cold Spring Harbor Laboratory Press, 1989, pp. 17.1-17.44).*
Jiz, Mario et al. "Pilot-Scale Production and Characterization of Paramyosin, a Vaccine Candidate for Schistosomiasis Japonica." Infection and Immunity. 76(7):3164-3169 (2008).
Chen, H. et al. "Vaccination of Domestic Pig with Recombinant Paramyosin Against Schistosoma Japonicum in China." Vaccine, Butterworth Scientific. 18(20):2142-2146 (2000).
Bergquist, N. et al. "Vacinne-linked Chemotherapy: Can Schistosomiasis Control Benefit from an Integrated Approach?" Trends in Parasitology, Elsevier Current Trends. 21(3):112-117 (2005).
McManus, D et al. "Recombinant Paramyosin (rec-Sj-97) Tested for Immunogenicity and Vaccine Efficacy Against Schistosoma Japonicum in Mice and Water Buffaloes." Vaccine. 20(5-6):870-878 (2001).
Kalinna, B.H. et al. "Engineering and Expression of a Full Length cDNA encoding Schistosoma Japonicum Paramyosin Purification of the Recombinant Protein and its Recognition by Infected Patient Sera." Acta Tropica. 65(2):111-115 (1997).
Jiz, Mario et al. "Pilot Scale Expression and Purification of Schistosoma Japoivicum Paramyosin," American Journal of Tropical Medicine and Hygiene. 77(5):96 (2007).

* cited by examiner

*Primary Examiner* — Brian J Gangle
(74) *Attorney, Agent, or Firm* — Mintz Levin Cohn Ferris Glovsky and Popeo, P.C.; Ingrid A. Beattie; Linyu L. Mitra (57) ABSTRACT

The method for large scale production of a full length Schistosomal paramyosin coiled coil dimer composition is carried out by providing a composition comprising recombinant paramyosin, contacting the composition with a strand separation agent to remove paramyosin fragments and other contaminants. The purified paramyosin is used in vaccines for humans and bovine animals to induce immunity against schistosomal infection.

11 Claims, 6 Drawing Sheets

FLOWCHART FOR THE EXPRESSION AND PURIFICATION OF Sj97

CLONING OF Sj97 INTO AN EXPRESSION VECTOR
(FULL-LENGTH *S. JAPONICUM* PARAMYOSIN cDNA SEQUENCE INSERTED INTO pET32 Xa/LIC VECTOR WITH THIOREDOXIN FUSION TAG) AND TRANSFECTION INTO AN EXPRESSION HOST (*E.COLI* STRAIN BL21)

↓

EXPRESSION IN A 10 LITER FERMENTOR
EQUIPPED WITH REGULATORS FOR TEMPERATURE, pH, FEED MEDIA, EXTERNAL OXYGEN, AND AGITATION
MEDIA: TERRIFIC BROTH SUPPLEMENTED WITH CARBENICILLIN AND $MgSO_4$
INDUCED AT LATE-LOGARITHMIC PHASE WITH 1mM IPTG FOR 5 HOURS
CELL CULTURE SPUN DOWN AT 6000 rpm FOR 30 MINUTES
TYPICAL YIELDS OF 750 GRAMS WET CELL PELLET PER 10L FERMENTATION

↓

EXTRACTION OF Sj97 FROM INCLUSION BODIES
*WASH 1*
500g WET CELL PELLET RESUSPENDED IN 5L OF PBS, 1% TRITON X-100 (octyl phenol ethoxylate) CELL DISRUPTION BY MICROFLUIDIZER, SPIN DOWN
*WASH 2*
RESUSPEND PELLET IN 3L OF PBS, CELL DISRUPTION, SPIN DOWN
*EXTRACTION*
BUFFER: 1L OF 8M UREA, 10 mM TRIS, 10 mM DTT pH 8.0
CELL DISRUPTION, MEMBRANE FILTRATION THROUGH 0.8 AND 0.45 μm
INCLUSION BODY PREP PRODUCT = 1L AT 6.5 mg/mL PROTEIN

↓

PURIFICATION OF rSj97 BY LIQUID CHROMATOGRAPHY
SEE DETAILS ON SUCCEEDING FLOWCHART

↓

FINAL PRODUCT PROCESSING
*CONCENTRATION BY TANGENTIAL FLOW FILTRATION*
SAMPLE: 400 mL POOLED rSj97 POST-CHROMATOGRAPHY
PRODUCT: 80 mL OF rSj97 AT 0.4 mg/mL
*SDS REMOVAL*
BUFFER: ADDITION OF SUCROSE TO 3% AND TWEEN-20 (POLYSORBATE 20) TO 0.005% INCUBATE IN THE COLD OVERNIGHT, SPIN DOWN AND FILTER 0.4um, 0.22um

*LYOPHILIZATION*
ALIQUOT INTO 1 mL VIALS, LABELED rSj97 FULL-LENGTH
LYOPHILIZE, STORE PRODUCTS IN -80°C
FINAL CONCENTRATION AT RESUSPENSION AT 0.28 mg/mL

Fig. 1

**FLOWCHART FOR THE EXPRESSION AND PURIFICATION OF Sj97
DETAIL OF CHROMATOGRAPHY PURIFICATION**

---

ANION EXCHANGE CHROMATOGRAPHY
COLUMN: MacroPrep HighQ, 50 μm (BIO-RAD) IN BPG 100/500, 2 L CV
BUFFER: 4M UREA, 10 mM TRIS, 1 mM DTT pH 8.0 ± 1M NaCl
GRADIENT: 0 TO 0.5M NaCl IN 5 CV
SAMPLE: 1L INCLUSION BODY EXTRACT
ELUATE: 2L POOL CONTAINING Sj97 AT 610 μg/mL

↓

HYDROXYAPATITE CHROMATOGRAPHY
COLUMN: CERAMIC HYDROXYAPATITE TYPE I, 20 μm (BIO-RAD) IN FineLine PILOT 35, 80 mL CV
BUFFER: 10 mM AND 500 mM POTASSIUM PHOSPHATE, 16 ppm $CaCl_2$, 1 mM DTT pH 7
GRADIENT: 10 to 500 mM K PHOSPHATE IN 10 CV
*RUN 1*
SAMPLE: 2L OF ANION EXCHANGE POOL
ELUATE: 400 mL POOL CONTAINING Sj97
*RUN 2*
SAMPLE: FLOWTHROUGH OF THE FIRST HYDROXYAPATITE RUN
ELUATE: 225 mL POOL CONTAINING Sj97
POOLED CHT RUN 1 & 2 ELUATES AT 815 μg/mL

↓

CONCENTRATION ANION EXCHANGE
*RUN 1*
COLUMN: MacroPrep HighQ, 50 μm (BIO-RAD) IN FineLine PILOT 35, 130 mL CV
BUFFER: 10 mM SODIUM PHOSPHATE pH 7.4 ± 300 mM NaCl
GRADIENT: 0 TO 300 mM NaCl IN 0 CV, UPFLOW
SAMPLE: POOL OF HYDROXYAPATITE ELUATES RUN 1 & 2, DILUTED 1:1 IN WATER
ELUATE: 125 mL POOL CONTAINING Sj97 AT 2.7 mg/mL
*RUN 2*
COLUMN: MacroPrep HighQ, 50 μm (BIO-RAD) IN HR 10/30, 20 mL CV
SAMPLE: EXCESS 150 mL OF concAnEx RUN 1, DILUTED 1:1 IN WATER
ELUATE: 40 mL POOL CONTAINING Sj97 AT>1.5 mg/mL

↓

SIZE EXCLUSION CHROMATOGRAPHY
COLUMN: SUPERDEX 200 (GEL FILTRATION COLUMN) PREP GRADE, 35 um IN 35/600 (PHARMACIA), 600 mL CV
BUFFER: 10 mM SODIUM PHOSPHATE, 0.3M NaCl, pH 7.4, 0.05% SDS
*RUN 1 TO 18*
SAMPLE: 5 mL OF concAEx RUN 1 ELUATE
ELUATE: 15 mL OF PURIFIED FULL-LENGTH rSj97 AT 100 μg/mL
*RUN 19 TO 26*
SAMPLE: 5 mL OF concAEx RUN 2 ELUATE
ELUATE: 15 mL OF PURIFIED FULL-LENGTH rSj97 AT 100 μg/mL

SCHISTOSOMA VACCINE

RELATED APPLICATIONS

This application is a national stage application, filed under 35 U.S.C. §371, of International Application No. PCT/US2008/012486, filed on Nov. 5, 2008, which claims the benefit of U.S. Ser. No. 61/002,070, filed on Nov. 5, 2007, the contents of each of which are incorporated herein by reference in their entirety.

GOVERNMENT SUPPORT

This invention was made with government support under NIH/NIAID R01-A148123 awarded by the National Institutes of Health. The government has certain rights in the invention.

INCORPORATION OF SEQUENCE LISTING

The contents of the text file named 21486585001 WOSEQLIST, which was created on Jan. 9, 2009 and is 8 KB in size, are hereby incorporated by reference in their entirety.

FIELD OF THE INVENTION

The invention relates to vaccine production.

BACKGROUND OF THE INVENTION

Schistosomiasis is a parasitic disease, the infectious agent of which was first identified in Egypt in 1851. Infection is widespread with a relatively low mortality rate, but a high morbidity rate, causing severe debilitating illness in millions of people.

Although candidate antigens for vaccine development have been identified, effective vaccines have not been produced. Delays in vaccine development have been due to difficulties in the scaling up of antigen production.

SUMMARY OF THE INVENTION

The invention provides a solution to the vexing problem of scaling up Schistosomial antigen production for vaccine preparation. The method for large scale production of a full length Schistosomal paramyosin coiled coil dimer composition is carried out by providing a composition comprising recombinant paramyosin, contacting the composition with a strand separation agent to yield a solution of paramyosin monomers, removing low molecular weight moieties from the solution of monomers, and removing the strand separation agent to yield purified full length Schistosomal paramyosin coiled dimer composition. The paramyosin is recombinant *Schistosoma japonicum* 97 (Sj97) or *Schistosoma mansoni* (Sm97). The method yields a preparation of full length paramyosin that is substantially purified from paramyosin fragments, e.g., carboxy-terminal fragments of paramyosin that often contaminate the preparation. A substantially pure preparation contains at least 85%, 90%, 95%, 98%, 99%, 100% full-length paramyosin (w/w). The preparation contains less than 5% paramyosin fragments or breakdown products (more preferably, the composition contains less than 4, 3, 2, 1% of such low molecular weight contaminants). Low molecular weight contaminants include paramyosin fragments, the molecular mass of which are less than 90, less than 75, less than 50, less than 35, less than 25, or less than 15 kDa.

A critical step is strand separation. The strand separation agent is a strong denaturant or detergent, e.g., urea (at least 5, 6, 7, 8, 9 M), or guanidium hydrochloride (5, 6, 7, 8, 9 M), optionally in the presence of heat (e.g., 45, 50, 55, 60, 65, 70 degrees C.). The strand separation agent is a detergent, e.g., a nonionic or ionic detergent. Preferably, the agent is an ionic detergent such as sodium dodecyl sulfate (SDS (at least 0.02, 0.03, 0.04, 0.05, 0.07%) or sarcosyl (N-lauryl sarcosine; at least 0.2, 0.3, 0.4, 0.5, 0.7%). Preferably, the detergent is not a nonionic detergent. Other strand separation agents include deoxycholic acid.

Compared to other methods of purifying paramyosin, the method described herein offers numerous advantages including higher purity and higher concentration of purified paramyosin. For example, the method yields at least 25 mg of purified paramyosin per 10 liters of culture. Another significant advantage of the method is that the paramyosin is present in a preferred antigenic form, i.e., its tertiary structure is a coiled coil as evidenced by its collagen and IgG binding. At least 80, 85, 90, 95, 98, 99, and up to 100% of the purified paramyosin is in the coiled structure. A paramyosin preparation in which the dimers are not in the coiled coil structure produced an attenuated immune response. Thus, the purified paramyosin composition described herein induces a superior immune response compared to earlier preparations.

Also within the invention is a vaccine comprising a pharmaceutically effective amount of a full length Schistosomal paramyosin coiled coil dimmer. The paramyosin in the vaccine preparation is substantially purified from a low molecular weight fragment of the protein. The vaccine further comprises an adjuvant such as alum (humans) or mannide oleate, and mineral oil (for veterinary use).

The invention further encompasses the use of a substantially purified full length Schistosomal paramyosin coiled coil dimmer that is purified from a low molecular weight fragment(s) of paramyosin in the manufacture of a vaccine for humans or bovine animals against a schistosomal infection.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, GenBank/NCBI accession numbers, patent applications, patents, and other references mentioned herein are incorporated by reference in their entirety. In the case of conflict, the present specification, including definitions, will control. In addition, the materials, methods, and examples are illustrative only and not intended to be limiting.

Other features and advantages of the invention will be apparent from the following detailed description and claims.

BRIEF DESCRIPTION OF THE DRAWINGS

FIG. 1 is a flow chart for the expression and purification of Sj97.

FIG. 2 is a flow chart showing details of the "Purification of rSj97 by Liquid Chromatography" step from FIG. 1.

FIG. 3 is a photocopy of an electrophoretic gel showing proteins obtained from a purification run of full length rSj97. Lane 1—inclusion body prep; Lane 2—pooled fractions from anion exchange; Lane 3—pooled fractions from CHT; Lane 4 pooled fractions from size exclusion chromatography.

FIG. 4 is photograph of an electrophoretic gel showing that rSj97 is greater than 95% pure. Lyophilized rSj97 was reconstituted and analyzed by SDS-PAGE under reducing conditions followed by colloidal Coomassie staining.

DETAILED DESCRIPTION

Schistosomiasis is endemic in 74 developing countries with more than 80% of infected people living in sub-Saharan Africa. The causative agent is a trematode flatworm (fluke) of the genus Schistosoma. S. haematobium is a prevalent and widespread species in Africa and the Middle East. S. intercalatum occurs in 10 countries in the rainforest belt of Africa. S. mansoni is found in Africa, and S. japonicum is found in the Pacific region including China and the Philippines. S. mekongi is found in limited areas of Laos and Cambodia.

Transmission occurs in freshwater when intermediate snail hosts release infective forms of the parasite. People are infected by contact with water where infected snails live. Larval forms of the parasites (known as cercariae), are released by the snails, and penetrate the skin of people in the water. The snails themselves become infected by another larval stage of the parasite, known as a miracidium, which develops from eggs passed out in the urine or feces of infected people.

Adult male and female schistosomes pair and live together in human blood vessels. The females release eggs, some of which are passed out in the urine or stools, but some eggs are trapped in body tissues. Some aspects of the disease are caused by immune reactions to eggs lodged in tissues. In urinary schistosomiasis, damage to the urinary tract is revealed by blood in the urine. Urination becomes painful and is accompanied by progressive damage to the bladder, ureters and then the kidneys. Bladder cancer may occur in advanced cases. In intestinal schistosomiasis (e.g., as a result of infection with S. mansoni, S. japonicum) disease is slower to develop. There is progressive enlargement of the liver and spleen, intestinal damage due to fibrotic lesions around eggs lodged in these tissues, and hypertension of the abdominal blood vessels. Bleeding from these vessels leads to blood in stools, and can be fatal. Functioning of organs such as spleen and kidneys becomes impaired. Bleeding from varicose veins in the esophagus is associated with intestinal schistosomiasis. Children are especially vulnerable to infection, which develops into chronic disease if not treated.

Schistosomal Paramyosin

Paramyosin, a 97 kDa myofibrillar protein, is a candidate vaccine antigen for prevention of infection with the human parasite Schistosoma mansoni. Active immunization with this antigen conferred resistance to infection by S. mansoni, and an anti-paramyosin monoclonal antibody conferred resistance to infection with S. japonicum. To determine if paramyosin would also induce protection against Schistosoma japonicum, purified paramyosin was made from S. japonicum adult worms. SDS-PAGE demonstrated a single protein with a molecular weight of 97 kDa. In four separate experiments, vaccination of mice with S. japonicum paramyosin without adjuvant induced significant resistance (62%-86%, all $p<0.001$) against cercarial challenge as compared to controls. Treatment with the denaturants SDS (0.5%) or Urea (8M) did not diminish this protective efficacy. These data indicate that S. japonicum paramyosin represents a viable candidate vaccine.

Paramyosin was cloned from a S. japonicum cDNA library. Affinity purified antibodies to this clone recognized an S. japonicum antigen of molecular weight 97 kDa, equivalent to the reported size of S. mansoni paramyosin. The deduced amino acid sequence of Sj97 shares 95% identity with Sm97.

As discussed above, Schistosoma japonicum paramyosin (Sj97) is a leading antigen for the production of vaccines against human schistosomiasis. However, development of paramyosin as a vaccine candidate ceased in the late 1990s due to the inability to develop robust pilot scale expression and purification protocols. This difficulty was highlighted in a review by Bergquist et al., who remarked that scale-up was "the stumbling block forcing the further development of two of the most promising vaccine candidates (paramyosin and MAP4) to be shelved" (Berquist et al, 2005, Trends Parasitol. 21:112-117).

The methods described herein solve the problems associated with earlier attempts at scaling up antigen production and successfully produce purified full-length recombinant Sj97 at large scale. The method involves using a standard and commercially available DNA vector (pET 32 Xa LIC) for expression. Purification involves 3 chromatography steps. The last and critical step of the process requires the use of an unusually strong denaturant (e.g., 0.05% SDS). A robust large scale production protocol for full-length rSj97 was developed. The production protocol for full-length rSj97 yields approximately 150 mg per 10 L fermenter run.

This method is suitable for large scale production of antigen for the preparation of vaccines for human schistosomiasis (200 million infections world wide with 600 million at risk) and for use as a bovine vaccine for several parasitic tapeworms. T-helper 2 (Th2) lymphocyte responses to Sj97 were associated with 30 to 41% decreased intensity of reinfection in humans.

The purified rSj97 produced as described herein was >95% pure as judged by sodium dodecyl sulfate-polyacrylamide gel electrophoretic analysis and was free of significant endotoxin contamination. Like native paramyosin, rSj97 adopts an alpha-helical coiled-coil tertiary structure and binds immunoglobulin and collagen. Naïve mice infected with S. japonicum produced anti-rSj97 immunoglobulin G (IgG) antibodies as early as 4 weeks postinfection, while sera collected from S. japonicum-infected individuals contain anti-rSj97 IgE antibodies.

Production of Recombinant Sj97 (rSj97)

The full length ORF of Sj97 was cloned into pET 32 Xa/LIC. This vector expresses full length Sj97 with an amino terminal thioredoxin fusion tag (108 aa). Recombinant full length Sj97 with and without a thioredoxin tage was purified as described below.

A master lot of the plasmid was prepared: the bulk was precipitated with $1/10^{th}$ vol of 3 M Na Acetate, and 0.7 vol of isopropanol and stored at −80 deg C., a sequencing concentration (90 ng/ul) was prepared in dH2O and stored at −80 deg C., an intermediate concentration (45 ng/ul) was prepared in dH2O and stored at −80 deg C. and a transformation concentration (10 ng/ul) was prepared in dH2O and stored at −80 deg C.

Fermentation. Ten ng of resulting plasmid was transformed into *E. coli* BL-21 (DE3) and plated in LB agar plates supplemented with 100 ug/mL carbenicillin. A single colony was inoculated in 5 ml of Terrific Broth supplemented with 100 ug/ml of carbenicillin for 8 hrs at 37 deg C. with shaking at 300 RPM. This culture was inoculated into 1 L of TB supplemented with 100 ug/ml of carbenicillin and grown O/N at 37 deg C. with shaking at 300 RPM. The O/N culture is inoculated into 8 L of TB supplemented with 100 ug/ml of carbenicillin and Antifoam 204 (typically 75 mls of a 1:2 dilution, Sigma) at 37 deg C. in a 14 L fermenter (Microferm, New Brunswick Scientific). The culture conditions are: oxygen sparging (10 L/min), pH stat at 7.0, feed rate of 50 ml of 30% glycerol, 9% Yeast extract/hr, T maintained at 37 deg C., agitation at 900 RPM. The culture is grown until an OD600 of 30 is reached and IPTG is added to a final concentration of 10 mM and growth is continued for 5 hours. The culture is harvested by centrifugation with a typical wet cell weight of 700-800 grams. Sj97 expressed in this system accumulated in the inclusion bodies following lysis on a continuous flow microfluidizer at 18,000 psi (Microfluidics model 110Y).

Harvest and inclusion body preparation. The cell culture is centrifuged at 6,000 RPM in a 6L rotor (Fiberlite, F6S-6x1000y) in a Sorval RC 3B centrifuge for 30 min at 4 deg C. The supernatant is discarded and the cell paste is weighed and stored at −80 deg C. Five hundred grams of cell paste are thawed and resuspended in 5 L of PBS, 1% TWEEN-20 (Polysorbate 20), pH 7.4. Cells are lysed by passage through a continuous flow microfluidizer at 18,000 psi (Microfluidics model 110Y). Lysate is centrifuged at 6,000 FPM in a 6 L rotor in a Sorval RC 3B centrifuge for 60 min at 4 deg C. The supernatant is discarded and the pellet is resuspended in 3 L of PBS, pH 7.4 and passed through a continuous flow microfluidizer at 18,000 psi (Microfluidics model 110Y). The lysate is centrifuged at 6,000 RPM in the 6 L rotor in a Sorval RC 3B centrifuge at 60 min at 4 deg C. The supernatant is discarded and inclusion bodies are dissolved in 1 L of 10 mM Tris, 8M Urea, 10 mM DTT pH 8.0.

Capture Step. Inclusion bodies are clarified by filtration sequentially through 0.8 uM and 0.45 uM vacuum filters. Filtrate is applied to a 2 L anion exchange column (Macro-Prep High Q, 50 um, BioRad) in a Pharmacia BPG 10/500 column using a Pharmacia BioPilot chromatography skid equipped with a SuperFrac collector. The column is washed with Buffer A: 10 mM Tris, 4M Urea, 1 mM DTT pH 8.0 and eluted with a linear gradient of 1M NaCl in Buffer A.

Figure 3:
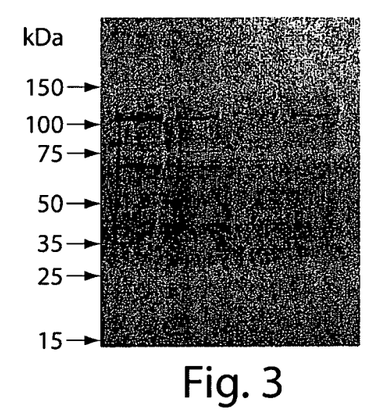

Intermediate Purification Step. Fractions containing rSj97 (typical vol=2 L) are pooled, divided in two and separately applied to an 80 mL ceramic hydroxyl appatite column (CHT type 1, 20 um, BioRad) in a Pharmacia FineLine Pilot 35 column. The column is washed with Buffer A: 10 mM potassium phosphate, 1 mM DTT, 16 ppm $CaCl_2$ pH 7.0 and eluted with a linear gradient to 500 mM potassium phosphate in Buffer A. Following intermediate purification, 2 major contaminants remained. (FIG. 3)

Concentration. Hydroxyapatite eluates containing Sj97 were pooled, diluted in 1:1 in Buffer A, and loaded into a 150 mL Anion Exchange column (MacroPrep Hi Q, 50 um, Biorad) in FineLine Pilot 35 pre-eq2uilibrated with Buffer A: 10 mM sodium phosphate pH 7.4. Concentration was achieved by step elution in Buffer B: 300 mM sodium chloride in Buffer A, pH 7.4 in an upflow direction. Tubes from the CHT step that contain lesser amounts of Sj97 were pooled and loaded in a similar Anion Exchange column at 20 mL column volume in HR 10/30 and concentrated in similar conditions.

Polishing Step. Lower molecular weight contaminants remain following intermediate purification. This contamination was a typical finding in earlier purification protocols for paramyosin (FIG. 3). Initial attempts to remove these contaminants using cation exchange, anion exchange, size exclusion, reverse phase, hydrophobic interaction and mixed mode chromatography all failed—the contaminants co-eluted with the full length paramyosin. MS based sequencing of the contaminants revealed that they were carboxy terminal portions of Sj97. The structure of paramyosins revealed that the paramyosin dimers which form the alpha-helical coiled coil are remarkably resistant to denaturation. Paramyosin strand separation only occurs with strong detergents, e.g., Guanidium Hydrochloride (Gu-HCl) concentrations about 7 M, or urea concentrations above 9 M with temperature at 60 deg C., or high concentration of an ionic detergent (e.g., 0.05% SDS). Strand renaturation was found to occur spontaneously after removal of the denaturants. To remove the contaminants that were participating in coiled coils with the full length protein, a polishing chromatography step with conditions capable of separating the monomers was employed.

SDS was added to the concentrated post-CHT sampled to a concentration of 0.05%. Size exclusion chromatography using SUPERDEX 200 (gel filtration column) prep grade (Pharmacia) was performed in a BioPilot 35/600 column in 10 mM sodium phosphate, 0.3M NaCl, and 0.05% SDS in ph 7.4. The volume of sample loaded was 5 mls. This process was repeated until the sample was exhausted (typically requires 25-30 runs).

Formulation and lyophilization. Fractions containing full length Sj97 were concentrated on a tangential flow filter (Minimate TFF Capsule, 5 kDA cutoff, Cat#OA005C12, Pall) at 25 mls/min of cross flow which produces 4 mls/min of filtrate from 400 mls to 80 mls over 80 minutes. Excess detergent was precipitated by overnight cold treatment in the presence of 0.005% TWEEN-20 (Polysorbate 20) and 3% sucrose, and removed by centrifugation at 10,000×g for 30 min at 4 deg C and filtered through 0.45 uM filters at 4 deg C. Sample is then sterile filtered through 0.2 uM filters and one mL aliquots of the product were dispensed into 3 mL polypropylene bottles and lyophilized (Advantage XL, Virtis).

Product analysis. Resuspension of lyophilized product in 1 mL of ultra pure water yielded 280 ug/mL of protein at 0.01% SDS concentration. Endotoxin levels were 0.07 EU/ml as assessed in an FDA approved chromogenic LAI based assay. Initial stability studies indicate no loss of protein concentration or protein breakdown when lyophilized, reconstituted material is stored in liquid state for over 1 month at 4 degrees Celsius. Flow charts of the protocol are shown in FIGS. 1-2.

Analysis of rSj97 Preparation

Lyophilized recombinant *S. japonicum* paramyosin (rSj97) was expressed in *E. coli* with N-terminal thioredoxin (109aa) fusion tag in 2 ml polypropylene vials sealed under nitrogen (500 torr). When reconstituted with one ml of sterile water for injection, each vial contains 280 ug/ml rSj97 (as determined by BCA method (Pierce, Rockford Ill.)). The yield was 70 vials of lyophilized material.
Sequence (First aa of Paramyosin is Underlined in Bold):

(SEQ ID NO: 1)

MSDKIIHLTDDSFDTDVLKADGAILVDFWAEWCGPCKMIAPILDEIADEYQGKLTVAKLNIDQNPGTAP

KYGIRGIPTLLLFKNGEVAATKVGALSKGQLKEFLDANLAGSGSGHMHHHHHSSGLVPRGSGMKET

AAAKFERQHMDSPDLGTGGGSGIEGRMMNHDTESHVKISRTIYRGVSPSTTRLESRVRELEDILDLERD

ARVRAERHAADLSYQVDALSERLDEAGGSTTQTQELLKRREMEINKLRKDLENANASLELAETSMRR

RHQTALNELSLEVENLQKQKGKAEKDKSHLIMEVDNVLGQLDGALKAKQSAESKLEGLDSQLNRLKT

LTDDLQRQLTELNNAKSRLTSENFELLHINQDYEAQILNYSKAKSSLESQVDDLKRSLDDESRNRFNLQ

AQLTSLQMDYDNLQAKYDEESEEASNLRNQVSKFNADIAALKSKFERELMSKTEEFEEMKRKLTMRIT

ELEDVAERERLKAVSLEKLKTKLTLEIKDLQSEIESLSLENGELIRRAKSAESLASDLQRRVDELTIEVNT

LTSQNNQLESENMRLKSLVNDLTDKNNALERENRQMNDQVKELKSSLRDANRRLTDLEALRSQLEAE

RDNLASALHDAEEALRDMDQKYQASQAALNHLKSEMEQRLRERDEELESLRKSTTRTIEELTVTITEM

EVKYKSELSRLKKRYESSIADLEIQLDATNKANANLMKENKNLAQRVKDLETFLDDERRLREAAENNL

QITEHKRIQLANEVEELRSAMENLERLRKHAETELEETQSRVSELTIQVNTLSNDKRRLEGDIGVMQAD

MDDAINAKQAAEDRATRLNNEVLRLADELRQEQENYKHAEALRKQLEIEIREITVKLEEAEAFATREG

RRMVQKLQARVRELEAEFDGESRRCKDALAQARKFERQYKELQTQAEDDRRMVLELQDLLDKTQMK

MKAYKRQLEEMEEVSQITMNKYRKAQQQIEEAEHRADMAERTVIVRRVGPGGRAVSVARELSVTSN

RGMRATSMM

The calculated molecular weight is 117.7 kDa, and estimated pI=5.23. The vials of white crystalline powder were stored at −80 deg C. To reconstitute, one ml of sterile water was added for injection and swirl gently. After reconstitution, the appearance of the solution was that of a clear, colorless liquid. When reconstituted with one ml of sterile water for injection, each vial contains 300 mM sodium chloride, 3% sucrose, 0.005% polysorbate 20, mM sodium.

Sterility. No growth at 5 days when reconstituted with one ml of sterile water for injection and assessed by BacT/Alert blood culture method for aerobic and anaerobic bacteria (Organon Teknika Corp., Durham, N.C.).

Endotoxin level. When reconstituted with one ml of sterile water for injection, each vial contains 0.07 EU per ml by colorimetric LAL method (Lonza Bioscience, Basel Switzerland).

Residual sodium dodecyl sulphate (SDS) concentration. When reconstituted with one ml of sterile water for injection, vial contains less than 0.01% SDS by a standard dye binding method (Rusconi et al., 2001, Analyt. Biochem. 295:31-37.

Figure 4:
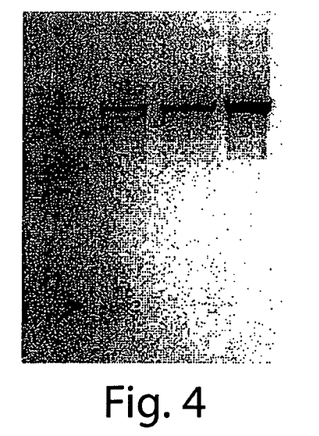

Electrophoretic mobility and purity. rSj97 migrates as a 113 kDa species with greater than 95% purity as assessed by densitometric analysis of 8-15% gradient SDS-PAGE separation under reducing conditions (FIG. 4). *S. japonicum* paramyosin without the thioredoxin fusion protein was purified using the same method of chromatographic purification.

Figure 8:
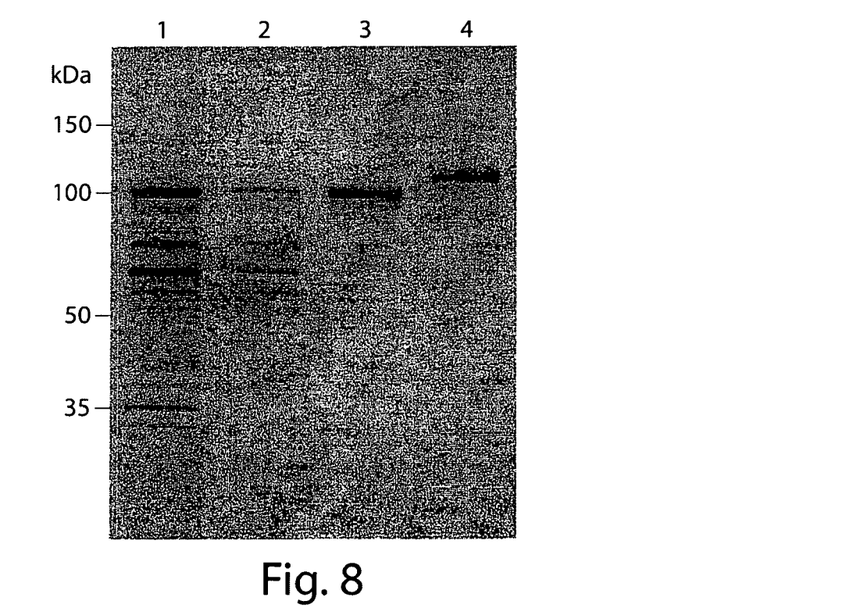
FIG. 8 is a photograph of an electrophoretic gel showing the results of chromatographic purification of rSj97 without a thioredoxin tag. Lane 1, inclusion body preparation; lane 2, anion exchange chromatography; lane 3, size exclusion chromatography; lane 4, purified S. japonicum paramyosin with the thioredoxin fusion protein.

Sj97 without a thioredoxin fusion tag (GenBank accession no. EU488865) was purified using starting material produced using a kanamycin-resistant plasmid. A pET-30 based plasmid construct containing paramyosin was expressed and purified as shown in FIG. 8.

Identity. LC-MS based sequencing identified 36 peptides from *S. japonicum* paramyosin (spanning 92% of the entire expected sequence) and 4 peptides from *E. coli* thioredoxin.

Figure 5:
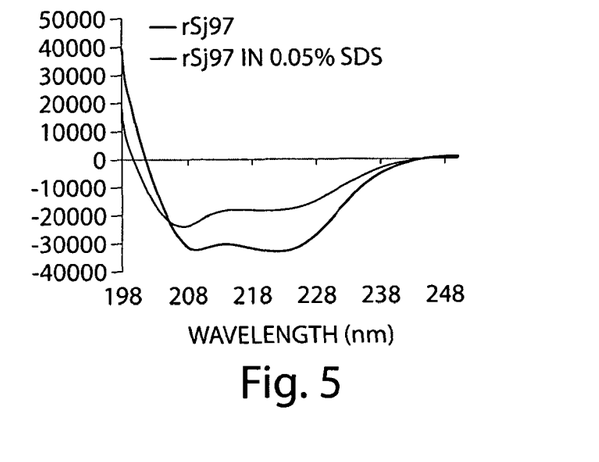
FIG. 5 is a line graph showing that Sj97 forms alpha helical coiled coils. When analyzed by circular dichroism at protein concentration of 70 ug/ml in 300 mM sodium chloride, 3% sucrose, 0.005% polysorbate 20, 10 mM sodium phosphate, pH 7.4, rSj97 contains 88% alpha helix as determined by method of Rohl and Baldwin and forms a coiled coil as defined by method of Thou (Theta220/Theta207>1).

Secondary structural analysis. When analyzed by circular dichroism at protein concentration of 70 ug/ml in 300 mM sodium chloride, 3% sucrose, 0.005% polysorbate 20, 10 mM sodium phosphate, pH 7.4, rSj97 contains 88% alpha helix as determined by method of Rohl and Baldwin (Rohl et al., 1997, Biochemistry 36:8435-8442) (FIG. 5).

Tertiary structural analysis. When analyzed by circular dichroism at protein concentration of 70 ug/ml in 300 mM sodium chloride, 3% sucrose, 0.005% polysorbate 20, mM sodium phosphate, pH 7.4, rSj97 forms a coiled coil as defined by method of Zhou (Theta$_{220}$/Theta$_{207}$>1) (Zhou et al., 1992, J. Biol. Chem. 267:2664-2670). (FIG. 5).

Figure 6:
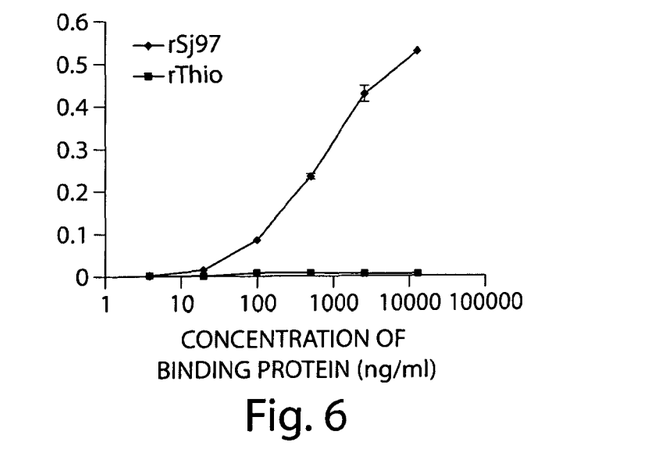
FIG. 6 is a line graph showing that rSj97 binds collagen. Collagen coated wells (type I and III) were incubated with increasing concentrations of rSj97 or thioredoxin, washed and probed with HRP labeled anti-thioredoxin.
Figure 7:
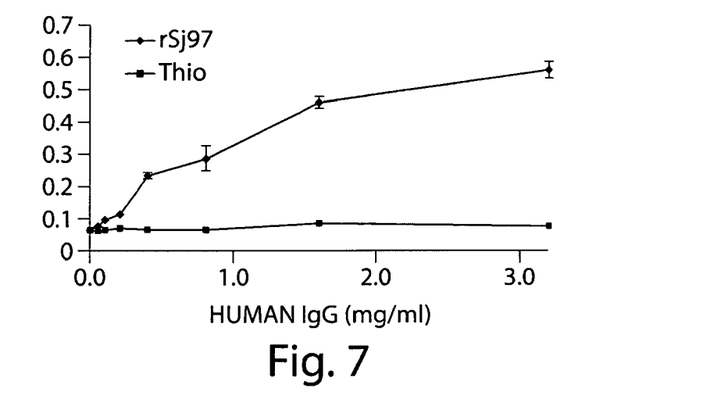
FIG. 7 is a line graph showing that rSj97 binds human IgG. rSj97 or thioredoxin coated wells were incubated with increasing concentrations of purified human IgG from North American donors. Wells were washed and probed with HRP labeled anti-human IgG.

Collagen binding and human IgG binding. rSj97 demonstrates significant binding when incubated in Type I and III collagen coated microtiter wells (Corgenix, Broomfield, Colo.) and probed with HRP labeled anti-thioredoxin antibody (FIG. 6). Thioredoxin alone demonstrates negligible binding in this assay. Human IgG binds to immobilized rSj97 (FIG. 7). Immobilized thioredoxin demonstrates negligible binding in this assay. These data indicate that the purified rSj97 in the final formulation is present in a coiled structure.

Stability. After reconstitution, rSj97 is stable when stored at 4 deg C. or −20 deg C. for greater than 1 month as assessed by 8-15% gradient SDS-PAGE separation under reducing conditions.

Vaccine Formulation

Purified vaccine antigens are adsorbed onto alum or combined with another adjuvant. Alum was chosen in this formulation, because it supports Th2 responses and remains the only adjuvant approved by the FDA for human use. Vaccine antigens are formulated at 0.5 mg protein adsorbed onto 50 ul of 2.0% ALHYDROGEL (Aluminium hydroxide gel) (Accurate Chemical, Westbury, N.Y.). This preparation contains approximately 0.5 mg of aluminum, (provided as amorphous aluminum hydroxyphosphate sulfate, previously referred to as aluminum hydroxide) in 1.0 mL of buffered saline. Vaccines are prepared from lyophilized protein stocks and aliquoted into single dose vials. Following reconstitution, they are transported and stored at 4 deg C without freezing (freezing may damage the colloidal structure of alum). The vaccine is suitable for human and veterinary use.

Veterinary Use

Bovine animals such as their water buffalo are a major reservoir for human transmission of schistosomiasis. In the Philippines and China, water buffalos utilized as draft animals are critical for agricultural productivity and contribute to a high prevalence of S. japonicum. The Chinese nationwide schistosomiasis survey in 1995 (covering both endemic and non-endemic areas) found that 9.6% of all buffalos were infected with S. japonicum, and infection is known to result in poor weight gain and therefore reduced work productivity in this species. The parasites move freely from buffalo to man, further supporting the importance of reducing/controlling infection in buffalo to reduce transmission to humans.

Purified full length, purified rSj97 is used to vaccinate bovine animals. A water buffalo immunization trial was carried out using rSj97 in a Th2 driving adjuvant (MONTANIDE™ ISA206, SEPPIC S.A., France) that is currently approved for veterinary use. MONTANIDE™ ISA 206 is an oily adjuvant composition of mannide oleate and mineral oil. Animals are injected subcutaneously, e.g., in the abdominal or neck area, with approximately 1.0 ml of vaccine. Four water buffalo were immunized with ISA206 alone and 6 water buffalo with LPS-free rSj97 (without thio tag) in ISA206. Each animal received 250 ug of antigen emulsified in 1.1 mls of ISA206 or 1.1 mls of ISA206 alone at 0, 4, and 8 weeks as a single subcutaneous injection in the middle third of the neck. Whole blood was collected 4 weeks after the third immunization, diluted 1:10 with RPMI, and cultured with 30 ug/ml rSj97 or RPMI alone. After 5 days culture supernatants were collected.

Figure 9:
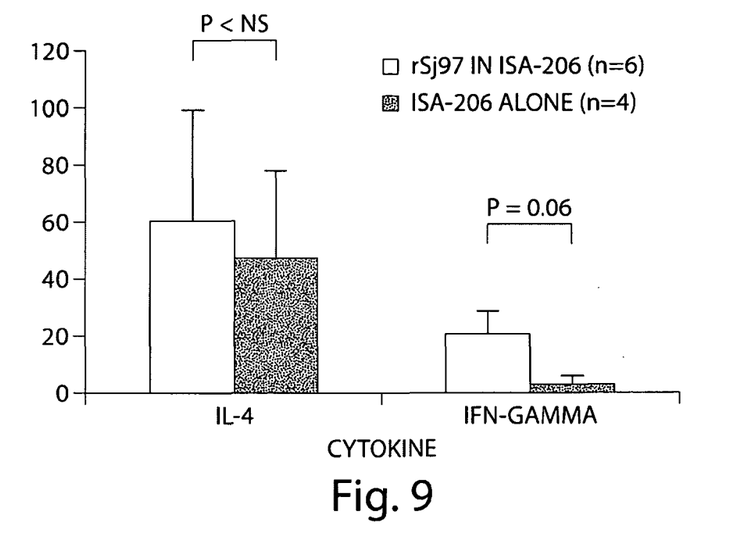
FIG. 9 is a bar graph showing that immunization of water buffaloes generates cytokine recall responses in whole blood cultures.

Using bovine specific capture and detection antibodies for IFN-gamma and IL-4 (Serotec), a multiplexed bead based cytokine detection assay was developed. After subtracting cytokine levels in un-stimulated wells, water buffalo immunized with rSj97 in ISA206 showed an increase in IL-4 production. Immunization further led to a 6.7 fold increase in IFN-gamma production in response to the recall antigen rSj97 compared to animals treated with adjuvant alone (FIG. 9). In summary, immunization with rSj97 in water buffalos generated cytokine recall responses in whole blood cultures. These data confirm that vaccination with the Sj97 preparation described herein generates a protective cellular responses in water buffalo using adjuvants approved for veterinary use.

Outcome of vaccination is also assessed by evaluating worm burden, body weight, reactogenicity, serum chemistry, hemograms, liver egg burden, antigen specific antibodies, and other immune indicators. For example, reduced worm burden and egg burden indicate clinical benefit. An increase in Th2 immune responses and production of antigen specific antibodies indicate a protective immune response against the Schistosomal pathogen.

Paramyosin is the Target of Protective IgE Responses in Humans

Figure 10:
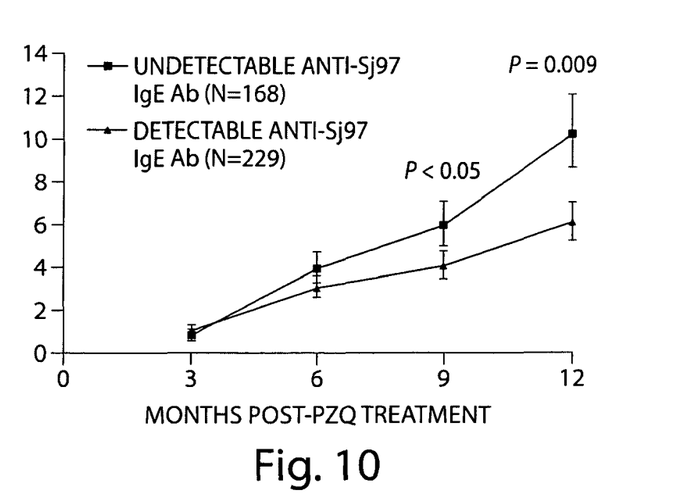
FIG. 10 is a line graph showing that human IgE responses to rSj97 are associated with resistance to infection in humans.

The relationship between rSj97 and resistance to reinfection was evaluated in humans. S. japonicum infected individuals were treated at baseline with Praziquantl (PZQ, Biltricide; an anthelmintic agent effective against flatworms) and followed with quarterly stool examination to quantify intensity of reinfection. Serum was obtained 4 weeks post treatment, and anti-rSj97 IgE antibody levels were measured using a bead-based assay (WormPlex). After subtracting fluorescence values for thioredoxin, responders were defined based on the mean plus 2 SD of the fluorescence values obtained in a group of ten unexposed North American controls. In repeated measures models, individuals with detectible IgE anti-Sj97 levels (n=229) had 41% lower intensity of reinfection measured 12 months after treatment than individuals with undetectible levels (n=168, P=0.009) after adjusting for potential confounders including directly observed water contact, village, age, sex, and baseline intensity of infection (FIG. 10). Responses to other components of the WormPlex (Sj67 and Sj22) were not associated with resistance in these analyses.

OTHER EMBODIMENTS

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

The invention claimed is:

1. A method, comprising providing a composition comprising recombinant paramyosin, contacting said composition with a strand separation agent to yield a solution of paramyosin monomers, removing low molecular weight moieties from said solution of monomers, and removing said strand separation agent to yield a product comprising purified full length Schistosomal paramyosin coiled coil dimer, wherein said paramyosin is selected from the group consisting of *Schistosoma japonicum* 97 (Sj97) and *Schistosoma mansoni* (Sm97), and wherein said strand separation agent comprises Guanidium Hydrochloride (Gu-HCl) with a concentration of about 7M, urea with a concentration of at least 9M, or an ionic detergent, wherein said ionic detergent comprises at least 0.02% (w/w) sodium dodecyl sulfate (SDS), at least 0.2% (w/w) N-lauryl sarcosine, or deoxycholic acid.

2. The method of claim 1, wherein said product comprises less than 5% (w/w) paramyosin fragments.

3. The method of claim 1, wherein said strand separation agent comprises an ionic detergent.

4. The method of claim 1, wherein said strand separation agent comprises at least 0.05% (w/w) sodium dodecyl sulfate.

5. The method of claim 1, wherein said method yields at least 25 mg of purified paramyosin per 10 liters.

6. The method of claim 1, wherein said strand separation agent comprises Gu-HCl with a concentration of about 7M.

7. The method of claim 1, wherein said strand separation agent comprises urea with a concentration of at least 9M.

8. The method of claim 1, wherein said strand separation agent comprises at least 0.02% SDS.

9. The method of claim 1, wherein said strand separation agent comprises N-lauryl sarcosine.

10. The method of claim 1, wherein said strand separation agent comprises deoxycholic acid.

11. A method, comprising providing a composition comprising recombinant paramyosin, contacting said composition with a strand separation agent to yield a solution of paramyosin monomers, removing low molecular weight moieties from said solution of monomers, and removing said strand separation agent to yield a product comprising purified full length Schistosomal paramyosin coiled coil dimer, wherein said paramyosin is selected from the group consisting of *Schistosoma japonicum* 97 (Sj97) and *Schistosoma mansoni* (Sm97), and wherein said strand separation agent comprises 8M urea with a temperature of at least 60° C.

* * * * *

SEQUENCE LISTING

```
<160> NUMBER OF SEQ ID NOS: 1

<210> SEQ ID NO 1
<211> LENGTH: 1028
<212> TYPE: PRT
<213> ORGANISM: Schistosoma japonicum

<400> SEQUENCE: 1

Met Ser Asp Lys Ile Ile His Leu Thr Asp Asp Ser Phe Asp Thr Asp
1               5                   10                  15

Val Leu Lys Ala Asp Gly Ala Ile Leu Val Asp Phe Trp Ala Glu Trp
            20                  25                  30

Cys Gly Pro Cys Lys Met Ile Ala Pro Ile Leu Asp Glu Ile Ala Asp
        35                  40                  45

Glu Tyr Gln Gly Lys Leu Thr Val Ala Lys Leu Asn Ile Asp Gln Asn
    50                  55                  60

Pro Gly Thr Ala Pro Lys Tyr Gly Ile Arg Gly Ile Pro Thr Leu Leu
65                  70                  75                  80
```

-continued

Leu Phe Lys Asn Gly Glu Val Ala Ala Thr Lys Val Gly Ala Leu Ser
            85                  90                  95

Lys Gly Gln Leu Lys Glu Phe Leu Asp Ala Asn Leu Ala Gly Ser Gly
        100                 105                 110

Ser Gly His Met His His His His His His Ser Ser Gly Leu Val Pro
        115                 120                 125

Arg Gly Ser Gly Met Lys Glu Thr Ala Ala Lys Phe Glu Arg Gln
        130                 135                 140

His Met Asp Ser Pro Asp Leu Gly Thr Gly Gly Ser Gly Ile Glu
145                 150                 155                 160

Gly Arg Met Met Asn His Asp Thr Glu Ser His Val Lys Ile Ser Arg
                165                 170                 175

Thr Ile Tyr Arg Gly Val Ser Pro Ser Thr Arg Leu Glu Ser Arg
                180                 185                 190

Val Arg Glu Leu Glu Asp Ile Leu Asp Leu Glu Arg Asp Ala Arg Val
        195                 200                 205

Arg Ala Glu Arg His Ala Ala Asp Leu Ser Tyr Gln Val Asp Ala Leu
        210                 215                 220

Ser Glu Arg Leu Asp Glu Ala Gly Gly Ser Thr Thr Gln Thr Gln Glu
225                 230                 235                 240

Leu Leu Lys Arg Arg Glu Met Glu Ile Asn Lys Leu Arg Lys Asp Leu
                245                 250                 255

Glu Asn Ala Asn Ala Ser Leu Glu Leu Ala Glu Thr Ser Met Arg Arg
        260                 265                 270

Arg His Gln Thr Ala Leu Asn Glu Leu Ser Leu Glu Val Glu Asn Leu
        275                 280                 285

Gln Lys Gln Lys Gly Lys Ala Glu Lys Asp Lys Ser His Leu Ile Met
        290                 295                 300

Glu Val Asp Asn Val Leu Gly Gln Leu Asp Gly Ala Leu Lys Ala Lys
305                 310                 315                 320

Gln Ser Ala Glu Ser Lys Leu Glu Gly Leu Asp Ser Gln Leu Asn Arg
                325                 330                 335

Leu Lys Thr Leu Thr Asp Asp Leu Gln Arg Gln Leu Thr Glu Leu Asn
                340                 345                 350

Asn Ala Lys Ser Arg Leu Thr Ser Glu Asn Phe Glu Leu Leu His Ile
        355                 360                 365

Asn Gln Asp Tyr Glu Ala Gln Ile Leu Asn Tyr Ser Lys Ala Lys Ser
        370                 375                 380

Ser Leu Glu Ser Gln Val Asp Asp Leu Lys Arg Ser Leu Asp Asp Glu
385                 390                 395                 400

Ser Arg Asn Arg Phe Asn Leu Gln Ala Gln Leu Thr Ser Leu Gln Met
                405                 410                 415

Asp Tyr Asp Asn Leu Gln Ala Lys Tyr Asp Glu Glu Ser Glu Ala
                420                 425                 430

Ser Asn Leu Arg Asn Gln Val Ser Lys Phe Asn Ala Asp Ile Ala Ala
        435                 440                 445

Leu Lys Ser Lys Phe Glu Arg Glu Leu Met Ser Lys Thr Glu Glu Phe
        450                 455                 460

Glu Glu Met Lys Arg Lys Leu Thr Met Arg Ile Thr Glu Leu Glu Asp
465                 470                 475                 480

Val Ala Glu Arg Glu Arg Leu Lys Ala Val Ser Leu Gly Lys Leu Lys
                485                 490                 495

```
Thr Lys Leu Thr Leu Glu Ile Lys Asp Leu Gln Ser Glu Ile Glu Ser
            500                 505                 510
Leu Ser Leu Glu Asn Gly Glu Leu Ile Arg Arg Ala Lys Ser Ala Glu
        515                 520                 525
Ser Leu Ala Ser Asp Leu Gln Arg Arg Val Asp Glu Leu Thr Ile Glu
    530                 535                 540
Val Asn Thr Leu Thr Ser Gln Asn Asn Gln Leu Glu Ser Glu Asn Met
545                 550                 555                 560
Arg Leu Lys Ser Leu Val Asn Asp Leu Thr Asp Lys Asn Asn Ala Leu
                565                 570                 575
Glu Arg Glu Asn Arg Gln Met Asn Asp Gln Val Lys Gly Leu Lys Ser
            580                 585                 590
Ser Leu Arg Asp Ala Asn Arg Leu Thr Asp Leu Glu Ala Leu Arg
        595                 600                 605
Ser Gln Leu Glu Ala Glu Arg Asp Asn Leu Ala Ser Ala Leu His Asp
    610                 615                 620
Ala Glu Glu Ala Leu Arg Asp Met Asp Gln Lys Tyr Gln Ala Ser Gln
625                 630                 635                 640
Ala Ala Leu Asn His Leu Lys Ser Glu Met Glu Gln Arg Leu Arg Glu
                645                 650                 655
Arg Asp Glu Glu Leu Glu Ser Leu Arg Lys Ser Thr Thr Arg Thr Ile
            660                 665                 670
Glu Glu Leu Thr Val Thr Ile Thr Glu Met Glu Val Lys Tyr Lys Ser
        675                 680                 685
Glu Leu Ser Arg Leu Lys Lys Arg Tyr Glu Ser Ser Ile Ala Asp Leu
    690                 695                 700
Glu Ile Gln Leu Asp Ala Thr Asn Lys Ala Asn Ala Asn Leu Met Lys
705                 710                 715                 720
Glu Asn Lys Asn Leu Ala Gln Arg Val Lys Asp Leu Glu Thr Phe Leu
                725                 730                 735
Asp Asp Glu Arg Arg Leu Arg Glu Ala Ala Glu Asn Asn Leu Gln Ile
            740                 745                 750
Thr Glu His Lys Arg Ile Gln Leu Ala Asn Glu Val Glu Glu Leu Arg
        755                 760                 765
Ser Ala Met Glu Asn Leu Glu Arg Leu Arg Lys His Ala Glu Thr Glu
    770                 775                 780
Leu Glu Glu Thr Gln Ser Arg Val Ser Glu Leu Thr Ile Gln Val Asn
785                 790                 795                 800
Thr Leu Ser Asn Asp Lys Arg Arg Leu Glu Gly Asp Ile Gly Val Met
                805                 810                 815
Gln Ala Asp Met Asp Asp Ala Ile Asn Ala Lys Gln Ala Ala Glu Asp
            820                 825                 830
Arg Ala Thr Arg Leu Asn Asn Glu Val Leu Arg Leu Ala Asp Glu Leu
        835                 840                 845
Arg Gln Glu Gln Glu Asn Tyr Lys His Ala Glu Ala Leu Arg Lys Gln
    850                 855                 860
Leu Glu Ile Glu Ile Arg Glu Ile Thr Val Lys Leu Glu Glu Ala Glu
865                 870                 875                 880
Ala Phe Ala Thr Arg Glu Gly Arg Arg Met Val Gln Lys Leu Gln Ala
                885                 890                 895
Arg Val Arg Glu Leu Glu Ala Glu Phe Asp Gly Glu Ser Arg Arg Cys
            900                 905                 910
```

-continued

```
Lys Asp Ala Leu Ala Gln Ala Arg Lys Phe Glu Arg Gln Tyr Lys Glu
    915                 920                 925

Leu Gln Thr Gln Ala Glu Asp Asp Arg Arg Met Val Leu Glu Leu Gln
    930                 935                 940

Asp Leu Leu Asp Lys Thr Gln Met Lys Met Lys Ala Tyr Lys Arg Gln
945                 950                 955                 960

Leu Glu Glu Met Glu Glu Val Ser Gln Ile Thr Met Asn Lys Tyr Arg
                965                 970                 975

Lys Ala Gln Gln Gln Ile Glu Glu Ala Glu His Arg Ala Asp Met Ala
                980                 985                 990

Glu Arg Thr Val Thr Val Arg Arg  Val Gly Pro Gly Gly  Arg Ala Val
        995                 1000                1005

Ser Val  Ala Arg Glu Leu Ser  Val Thr Ser Asn Arg  Gly Met Arg
    1010                 1015                1020

Ala Thr  Ser Met Met
    1025
```